United States Patent
Lazdunski et al.

(10) Patent No.: US 6,875,599 B2
(45) Date of Patent: Apr. 5, 2005

(54) MAMMALIAN SECRETED GROUP III PHOSPHOLIPASE $A_2$

(75) Inventors: Michel Lazdunski, Nice (FR); Gérard Lambeau, Blausasc (FR); Emmanuel Valentin, Antibes (FR)

(73) Assignee: Centre National de la Recherche Scientifique - CNRS, Paris (FR)

( * ) Notice: Subject to any disclaimer, the term of this patent is extended or adjusted under 35 U.S.C. 154(b) by 0 days.

(21) Appl. No.: 09/781,100

(22) Filed: Feb. 9, 2001

(65) Prior Publication Data

US 2002/0037572 A1 Mar. 28, 2002

Related U.S. Application Data

(60) Provisional application No. 60/181,765, filed on Feb. 11, 2000.

(51) Int. Cl.[7] .............................. C12N 9/20; C07H 21/04
(52) U.S. Cl. ......................... 435/198; 536/23.2; 435/4; 435/6; 435/183
(58) Field of Search ................................. 435/198, 4, 6, 435/183, 440; 536/23.2, 23.1; 530/350

(56) References Cited

PUBLICATIONS

Valentin et al. Novel human secreated phospholipase A2 with homology to the group III bee venom enzyme. The Journal of Biol. Chem. vol., 276, No. 11, Mar. 17, 2000, pp. 7492–7496.*

* cited by examiner

Primary Examiner—Manjunath Rao
Assistant Examiner—Yong Pak
(74) Attorney, Agent, or Firm—DLA Piper Rudnick Gray Cary US LLP

(57) ABSTRACT

The present invention concerns DNA and peptide sequence encoding a mammalian secreted group III $sPLA_2$ and more particularly a human secreted group III (hGIII) $sPLA_2$. The invention also concerns the use of this secreted group III $sPLA_2$ in methods for screening various chemical compounds.

1 Claim, 4 Drawing Sheets

FIG. 2

SEQUENCE LISTING

<160> NUMBER OF SEQ ID NOS: 10

<210> SEQ ID NO 1
<211> LENGTH: 2719
<212> TYPE: DNA
<213> ORGANISM: Homo sapiens
<220> FEATURE:
<221> NAME/KEY: CDS
<222> LOCATION: (254)..(1780)

<400> SEQUENCE: 1

```
atgggggcgt gggccctggc aagtgcactc ctcagccaat cagcgtcctg cccggctggt    60
ggattcggtt acaagcccaa gatcacccca tactccagcc tctttcctcc tcctcccgca   120
gctccattca ttggtcccgc cgcaccgggc ctgctgggct ccgcttccgt tccactgctc   180
agctgccgcc tggtggggcc accaagggca ggcatcccag gggctttgtc tgactggact   240
gggccagtgc aga atg ggg gtt cag gca ggg ctg ttt ggg atg ctg ggc      289
              Met Gly Val Gln Ala Gly Leu Phe Gly Met Leu Gly
                1               5                  10
```

```
ttc ctg ggg gtg gcc ctg ggg ggc tcc cct gcc ctc cgc tgg tac agg     337
Phe Leu Gly Val Ala Leu Gly Gly Ser Pro Ala Leu Arg Trp Tyr Arg
         15                  20                  25 acc tcc tgc cac ttg acc aag gcc gtc cct ggc aac cca ctg ggg tac     385
Thr Ser Cys His Leu Thr Lys Ala Val Pro Gly Asn Pro Leu Gly Tyr
     30                  35                  40 ctg agc ttc ctg gcc aag gat gct cag gga ctg gcc ctg atc cat gcc     433
Leu Ser Phe Leu Ala Lys Asp Ala Gln Gly Leu Ala Leu Ile His Ala
 45                  50                  55                  60 cgc tgg gat gcg cat agg agg ctg cag gca tgt agc tgg gag gat gag    481
Arg Trp Asp Ala His Arg Arg Leu Gln Ala Cys Ser Trp Glu Asp Glu
                 65                  70                  75 ccg gag ctc acc gca gcc tac ggt gct ctc tgt gct cat gag act gcc    529
Pro Glu Leu Thr Ala Ala Tyr Gly Ala Leu Cys Ala His Glu Thr Ala
             80                  85                  90 tgg ggc tcc ttc atc cac acc ccc gga ccc gag ctg cag aga gca ctg    577
Trp Gly Ser Phe Ile His Thr Pro Gly Pro Glu Leu Gln Arg Ala Leu
         95                 100                 105 gcc act ctt cag agt cag tgg gag gca tgc cga gcg ctt gag gag agt    625
Ala Thr Leu Gln Ser Gln Trp Glu Ala Cys Arg Ala Leu Glu Glu Ser
    110                 115                 120 cca gca ggg gcc agg aag aag cga gca gca ggg cag agt gga gtc cct    673
Pro Ala Gly Ala Arg Lys Lys Arg Ala Ala Gly Gln Ser Gly Val Pro
125                 130                 135                 140 ggt gga ggg cac cag cga gag aag aga gga tgg acc atg cct ggc aca    721
Gly Gly Gly His Gln Arg Glu Lys Arg Gly Trp Thr Met Pro Gly Thr
                145                 150                 155 ctg tgg tgt gga gtt gga gat tct gct ggg aac tcc tcg gag ctg ggg    769
Leu Trp Cys Gly Val Gly Asp Ser Ala Gly Asn Ser Ser Glu Leu Gly
            160                 165                 170 gtc ttc cag gga cct gat ctc tgt tgc cgg gaa cat gac cgc tgc cca    817
Val Phe Gln Gly Pro Asp Leu Cys Cys Arg Glu His Asp Arg Cys Pro
        175                 180                 185 cag aac atc tca ccc ttg cag tac aac tat ggc atc cga aac tac cga    865
Gln Asn Ile Ser Pro Leu Gln Tyr Asn Tyr Gly Ile Arg Asn Tyr Arg
    190                 195                 200 ttc cac acc atc tcc cac tgt gac tgt gac acc agg ttt cag caa tgc    913
Phe His Thr Ile Ser His Cys Asp Cys Asp Thr Arg Phe Gln Gln Cys
205                 210                 215                 220 cta cag aat cag cac gac tcc atc tcg gac atc gtg ggc gtg gcc ttc    961
Leu Gln Asn Gln His Asp Ser Ile Ser Asp Ile Val Gly Val Ala Phe
                225                 230                 235 ttc aac gtg ctg gag atc ccc tgc ttt gtg ctg gag gag cag gag gcg   1009
Phe Asn Val Leu Glu Ile Pro Cys Phe Val Leu Glu Glu Gln Glu Ala
            240                 245                 250 tgt gtg gcg tgg tac tgg tgg ggc ggg tgt agg atg tac ggc aca gtg   1057
Cys Val Ala Trp Tyr Trp Trp Gly Gly Cys Arg Met Tyr Gly Thr Val
        255                 260                 265
```

```
ccc ctc gct cgc ctg cag ccc agg acc ttc tac aat gcc tcc tgg agc      1105
Pro Leu Ala Arg Leu Gln Pro Arg Thr Phe Tyr Asn Ala Ser Trp Ser
    270             275                 280 tcc cgg gcc acc tcc cca act ccc agc tcc cgg agc cca gcc cct ccc      1153
Ser Arg Ala Thr Ser Pro Thr Pro Ser Ser Arg Ser Pro Ala Pro Pro
285             290                 295                 300 aag cct cga cag aag cag cac ctt cgg aag ggg cca cca cat cag aaa      1201
Lys Pro Arg Gln Lys Gln His Leu Arg Lys Gly Pro Pro His Gln Lys
                305                 310                 315 ggg tcc aag cgc ccc agc aaa gcc aac acc aca gcc ctc cag gac cct      1249
Gly Ser Lys Arg Pro Ser Lys Ala Asn Thr Thr Ala Leu Gln Asp Pro
            320                 325                 330 atg gtc tct ccc agg ctt gat gtg gcc ccc aca ggc ctc cag ggc cca      1297
Met Val Ser Pro Arg Leu Asp Val Ala Pro Thr Gly Leu Gln Gly Pro
        335                 340                 345 cag ggt ggc cta aaa cct cag ggt gcc cgc tgg gtc tgc cgc agc ttc      1345
Gln Gly Gly Leu Lys Pro Gln Gly Ala Arg Trp Val Cys Arg Ser Phe
    350                 355                 360 cgc cgc cac ctg gac cag tgt gag cac cag att ggg ccc cgg gaa atc      1393
Arg Arg His Leu Asp Gln Cys Glu His Gln Ile Gly Pro Arg Glu Ile
365                 370                 375                 380 gag ttc cag ctg ctc aac agc gcc caa gag ccc ctc ttc cac tgc aac      1441
Glu Phe Gln Leu Leu Asn Ser Ala Gln Glu Pro Leu Phe His Cys Asn
                385                 390                 395 tgc acg cgc cgt ctg gca cgc ttc ctg agg ctc cac agc cca ccc gag      1489
Cys Thr Arg Arg Leu Ala Arg Phe Leu Arg Leu His Ser Pro Pro Glu
            400                 405                 410 gtt acc aac atg ctt tgg gag ctg ctg ggc aca acc tgc ttc aag ctg      1537
Val Thr Asn Met Leu Trp Glu Leu Leu Gly Thr Thr Cys Phe Lys Leu
        415                 420                 425 gcc cct cca ctg gac tgt gtg gaa ggc aaa aac tgt tcc aga gac cct      1585
Ala Pro Pro Leu Asp Cys Val Glu Gly Lys Asn Cys Ser Arg Asp Pro
    430                 435                 440 agg gcc atc agg gtg tca gcc cgg cac ttg cgg agg ctt cag cag agg      1633
Arg Ala Ile Arg Val Ser Ala Arg His Leu Arg Arg Leu Gln Gln Arg
445                 450                 455                 460 cga cac cag ctc cag gat aaa ggc aca gat gag agg cag cca tgg cct      1681
Arg His Gln Leu Gln Asp Lys Gly Thr Asp Glu Arg Gln Pro Trp Pro
                465                 470                 475 tca gag ccc ctg aga ggc ccc atg tca ttc tac aac cag tgc ctg cag      1729
Ser Glu Pro Leu Arg Gly Pro Met Ser Phe Tyr Asn Gln Cys Leu Gln
            480                 485                 490 cta acc cag gca gcc agg aga ccc gac agg cag cag aag tcc tgg agc      1777
Leu Thr Gln Ala Ala Arg Arg Pro Asp Arg Gln Gln Lys Ser Trp Ser
        495                 500                 505 cag tgacctcagt ttcagctttc ctgggcacca gcctggacct tgcccatggc          1830
Gln tatgccaagc ttgggaatc tcagcctccc ctccgtaggt tagactgaag catggcagag    1890
gctgttgtgg acaatcaaga ggatgaatgg ggggatctca aggcccaaat gctggaccac   1950
atctcctgct gttctgggta accttgagct atgtatgaca caactcttct atgcctggat   2010
gtggtgttca ggaagctcat tctgatgccc tgggctttgg ccttgccagg gaacttcaca   2070
tacagatgag aatggggaaa gggtaactta ttgcagcagc cccaggcagt accaggagga   2130
ggtacatgta tgtccgtgtt gcaaaaataa tacatgcctc aaaaacctgc ctaggggagc   2190
cctagtgcct gggtgctgtg gcctgaggta gcaggtggga agttagggat gtcacagaaa   2250
tgtctgtgtc tgaatccagg attggggtgg gtgttggaga gggctttcag ctcccctcct   2310
```

```
cccagggggg cctcttttt taacggctgc cgtgcccttc ctggcccagc cctaaaccta    2370
aattcaaatc tcctccatgc ctttgcgcaa aggacctccc tcttgcactc taagccttag    2430
tttcctcctc taaaaaaagg gggtctctaa acaggagcta cctcataggg ttgttgagga    2490
ttaagtgaac caatacatat acagtgctta gcacttaata agtattcccc cctgcgacac    2550
ctagctgaac tatggtttgg tgtctgatct tgagaggttg atgtaacctt ttaaaggcct    2610
cagttcgctc acctgtgaaa tgggtctaag aatagcactg atctcacagg gttgtgatgc    2670
agattaaagg agatggcatg tgtaatgaaa aaaaaaaaa aaaaaaaa                   2719
```

<210> SEQ ID NO 2
<211> LENGTH: 509
<212> TYPE: PRT
<213> ORGANISM: Homo sapiens

<400> SEQUENCE: 2

```
Met Gly Val Gln Ala Gly Leu Phe Gly Met Leu Gly Phe Leu Gly Val
  1               5                  10                  15

Ala Leu Gly Gly Ser Pro Ala Leu Arg Trp Tyr Arg Thr Ser Cys His
             20                  25                  30

Leu Thr Lys Ala Val Pro Gly Asn Pro Leu Gly Tyr Leu Ser Phe Leu
         35                  40                  45

Ala Lys Asp Ala Gln Gly Leu Ala Leu Ile His Ala Arg Trp Asp Ala
     50                  55                  60

His Arg Arg Leu Gln Ala Cys Ser Trp Glu Asp Glu Pro Glu Leu Thr
 65                  70                  75                  80

Ala Ala Tyr Gly Ala Leu Cys Ala His Glu Thr Ala Trp Gly Ser Phe
                 85                  90                  95

Ile His Thr Pro Gly Pro Glu Leu Gln Arg Ala Leu Ala Thr Leu Gln
            100                 105                 110

Ser Gln Trp Glu Ala Cys Arg Ala Leu Glu Glu Ser Pro Ala Gly Ala
        115                 120                 125

Arg Lys Lys Arg Ala Ala Gly Gln Ser Gly Val Pro Gly Gly Gly His
    130                 135                 140

Gln Arg Glu Lys Arg Gly Trp Thr Met Pro Gly Thr Leu Trp Cys Gly
145                 150                 155                 160

Val Gly Asp Ser Ala Gly Asn Ser Ser Glu Leu Gly Val Phe Gln Gly
                165                 170                 175

Pro Asp Leu Cys Cys Arg Glu His Asp Arg Cys Pro Gln Asn Ile Ser
            180                 185                 190

Pro Leu Gln Tyr Asn Tyr Gly Ile Arg Asn Tyr Arg Phe His Thr Ile
        195                 200                 205

Ser His Cys Asp Cys Asp Thr Arg Phe Gln Gln Cys Leu Gln Asn Gln
    210                 215                 220

His Asp Ser Ile Ser Asp Ile Val Gly Val Ala Phe Asn Val Leu
225                 230                 235                 240

Glu Ile Pro Cys Phe Val Leu Glu Gln Glu Ala Cys Val Ala Trp
                245                 250                 255

Tyr Trp Trp Gly Gly Cys Arg Met Tyr Gly Thr Val Pro Leu Ala Arg
            260                 265                 270

Leu Gln Pro Arg Thr Phe Tyr Asn Ala Ser Trp Ser Ser Arg Ala Thr
        275                 280                 285

Ser Pro Thr Pro Ser Ser Arg Ser Pro Ala Pro Pro Lys Pro Arg Gln
    290                 295                 300
```

```
Lys Gln His Leu Arg Lys Gly Pro Pro His Gln Lys Gly Ser Lys Arg
305                 310                 315                 320

Pro Ser Lys Ala Asn Thr Thr Ala Leu Gln Asp Pro Met Val Ser Pro
                325                 330                 335

Arg Leu Asp Val Ala Pro Thr Gly Leu Gln Gly Pro Gln Gly Gly Leu
            340                 345                 350

Lys Pro Gln Gly Ala Arg Trp Val Cys Arg Ser Phe Arg Arg His Leu
        355                 360                 365

Asp Gln Cys Glu His Gln Ile Gly Pro Arg Glu Ile Glu Phe Gln Leu
    370                 375                 380

Leu Asn Ser Ala Gln Glu Pro Leu Phe His Cys Asn Cys Thr Arg Arg
385                 390                 395                 400

Leu Ala Arg Phe Leu Arg Leu His Ser Pro Pro Glu Val Thr Asn Met
                405                 410                 415

Leu Trp Glu Leu Leu Gly Thr Thr Cys Phe Lys Leu Ala Pro Pro Leu
            420                 425                 430

Asp Cys Val Glu Gly Lys Asn Cys Ser Arg Asp Pro Arg Ala Ile Arg
        435                 440                 445

Val Ser Ala Arg His Leu Arg Arg Leu Gln Gln Arg Arg His Gln Leu
    450                 455                 460

Gln Asp Lys Gly Thr Asp Glu Arg Gln Pro Trp Pro Ser Glu Pro Leu
465                 470                 475                 480

Arg Gly Pro Met Ser Phe Tyr Asn Gln Cys Leu Gln Leu Thr Gln Ala
                485                 490                 495

Ala Arg Arg Pro Asp Arg Gln Gln Lys Ser Trp Ser Gln
            500                 505

<210> SEQ ID NO 3
<211> LENGTH: 141
<212> TYPE: PRT
<213> ORGANISM: Homo sapiens

<400> SEQUENCE: 3

Gly Trp Thr Met Pro Gly Thr Leu Trp Cys Gly Val Gly Asp Ser Ala
1               5                   10                  15

Gly Asn Ser Ser Glu Leu Gly Val Phe Gln Gly Pro Asp Leu Cys Cys
                20                  25                  30

Arg Glu His Asp Arg Cys Pro Gln Asn Ile Ser Pro Leu Gln Tyr Asn
            35                  40                  45

Tyr Gly Ile Arg Asn Tyr Arg Phe His Thr Ile Ser His Cys Asp Cys
        50                  55                  60

Asp Thr Arg Phe Gln Gln Cys Leu Gln Asn Gln His Asp Ser Ile Ser
65                  70                  75                  80

Asp Ile Val Gly Val Ala Phe Phe Asn Val Leu Glu Ile Pro Cys Phe
                85                  90                  95

Val Leu Glu Glu Gln Glu Ala Cys Val Ala Trp Tyr Trp Trp Gly Gly
                100                 105                 110

Cys Arg Met Tyr Gly Thr Val Pro Leu Ala Arg Leu Gln Pro Arg Thr
            115                 120                 125

Phe Tyr Asn Ala Ser Trp Ser Ser Arg Ala Thr Ser Pro
        130                 135                 140

<210> SEQ ID NO 4
<211> LENGTH: 142
<212> TYPE: PRT
<213> ORGANISM: Heloderma suspectum
```

-continued

<400> SEQUENCE: 4

Gly Ala Phe Ile Met Pro Gly Thr Leu Trp Cys Gly Ala Gly Asn Ala
1               5                   10                  15

Ala Ser Asp Tyr Ser Gln Leu Gly Thr Glu Lys Asp Thr Asp Met Cys
            20                  25                  30

Cys Arg Asp His Asp His Cys Glu Asn Trp Ile Ser Ala Leu Glu Tyr
        35                  40                  45

Lys His Gly Met Arg Asn Tyr Tyr Pro Ser Thr Ile Ser His Cys Asp
    50                  55                  60

Cys Asp Asn Gln Phe Arg Ser Cys Leu Met Lys Leu Lys Asp Gly Thr
65                  70                  75                  80

Ala Asp Tyr Val Gly Gln Thr Tyr Phe Asn Val Leu Lys Ile Pro Cys
                85                  90                  95

Phe Glu Leu Glu Glu Gly Glu Gly Cys Val Asp Trp Asn Phe Trp Leu
            100                 105                 110

Glu Cys Thr Glu Ser Lys Ile Met Pro Val Ala Lys Leu Val Ser Ala
        115                 120                 125

Ala Pro Tyr Gln Ala Gln Ala Glu Thr Gln Ser Gly Glu Gly
    130                 135                 140

<210> SEQ ID NO 5
<211> LENGTH: 141
<212> TYPE: PRT
<213> ORGANISM: Heloderma suspectum

<400> SEQUENCE: 5

Gly Ala Phe Ile Met Pro Gly Thr Leu Trp Cys Gly Ala Gly Asn Ala
1               5                   10                  15

Ala Ser Asp Tyr Ser Gln Leu Gly Thr Glu Lys Asp Thr Asp Met Cys
            20                  25                  30

Cys Arg Asp His Asp His Cys Ser Asp Thr Met Ala Ala Leu Glu Tyr
        35                  40                  45

Lys His Gly Met Arg Asn Tyr Arg Pro His Thr Val Ser His Cys Asp
    50                  55                  60

Cys Asp Asn Gln Phe Arg Ser Cys Leu Met Asn Val Lys Asp Arg Thr
65                  70                  75                  80

Ala Asp Leu Val Gly Met Thr Tyr Phe Thr Val Leu Lys Ile Ser Cys
                85                  90                  95

Phe Glu Leu Glu Glu Gly Glu Gly Cys Val Asp Asn Asn Phe Ser Gln
            100                 105                 110

Gln Cys Thr Lys Ser Glu Ile Met Pro Val Ala Lys Leu Val Ser Ala
        115                 120                 125

Ala Pro Tyr Gln Ala Gln Ala Glu Thr Gln Ser Gly Glu
    130                 135                 140

<210> SEQ ID NO 6
<211> LENGTH: 134
<212> TYPE: PRT
<213> ORGANISM: Apis mellifera

<400> SEQUENCE: 6

Ile Thr Tyr Pro Gly Thr Leu Trp Cys Gly His Gly Asn Lys Ser Ser
1               5                   10                  15

Gly Pro Asn Glu Leu Gly Arg Phe Lys His Thr Asp Ala Cys Cys Arg
            20                  25                  30

```
Thr His Asp Met Cys Pro Asp Val Met Ser Ala Gly Glu Ser Lys His
        35                  40                  45

Gly Leu Thr Asn Thr Ala Ser His Thr Arg Leu Ser Cys Asp Cys Asp
    50                  55                  60

Asp Lys Phe Tyr Asp Cys Leu Lys Asn Ser Ala Asp Thr Ile Ser Ser
65                  70                  75                  80

Tyr Phe Val Gly Lys Met Tyr Phe Asn Leu Ile Asp Thr Lys Cys Tyr
                85                  90                  95

Lys Leu Glu His Pro Val Thr Gly Cys Gly Glu Arg Thr Glu Gly Arg
                100                 105                 110

Cys Leu His Tyr Thr Val Asp Lys Ser Lys Pro Lys Val Tyr Gln Trp
            115                 120                 125

Phe Asp Leu Arg Lys Tyr
        130
```

<210> SEQ ID NO 7
<211> LENGTH: 136
<212> TYPE: PRT
<213> ORGANISM: Pandinus imperator

<400> SEQUENCE: 7

```
Thr Met Trp Gly Thr Lys Trp Cys Gly Ser Gly Asn Glu Ala Thr Asp
1               5                   10                  15

Ile Ser Glu Leu Gly Tyr Trp Ser Asn Leu Asp Ser Cys Cys Arg Thr
                20                  25                  30

His Asp His Cys Asp Asn Ile Pro Ser Gly Gln Thr Lys Tyr Gly Leu
            35                  40                  45

Thr Asn Glu Gly Lys Tyr Thr Met Met Asn Cys Lys Cys Glu Thr Ala
        50                  55                  60

Phe Glu Gln Cys Leu Arg Asn Val Thr Gly Gly Met Glu Gly Pro Ala
65                  70                  75                  80

Ala Gly Phe Val Arg Lys Thr Tyr Phe Asp Leu Tyr Gly Asn Gly Cys
                85                  90                  95

Tyr Asn Val Gln Cys Pro Ser Gln Arg Arg Leu Ala Arg Ser Glu Glu
                100                 105                 110

Cys Pro Asp Gly Val Ala Thr Tyr Thr Gly Glu Ala Gly Tyr Gly Ala
            115                 120                 125

Trp Ala Ile Asn Lys Leu Asn Gly
        130                 135
```

<210> SEQ ID NO 8
<211> LENGTH: 136
<212> TYPE: PRT
<213> ORGANISM: Bombus pennsylvanicus

<400> SEQUENCE: 8

```
Ile Ile Tyr Pro Gly Thr Leu Trp Cys Gly Asn Gly Asn Ile Ala Asn
1               5                   10                  15

Gly Thr Asn Glu Leu Gly Leu Trp Lys Glu Thr Asp Ala Cys Cys Arg
                20                  25                  30

Thr His Asp Met Cys Pro Asp Ile Ile Glu Ala His Gly Ser Lys His
            35                  40                  45

Gly Leu Thr Asn Pro Ala Asp Tyr Thr Arg Leu Asn Cys Glu Cys Asp
        50                  55                  60

Glu Glu Phe Arg His Cys Leu His Asn Ser Gly Asp Ala Val Ser Ala
65                  70                  75                  80
```

```
Ala Phe Val Gly Arg Thr Tyr Phe Thr Ile Leu Gly Thr Gln Cys Phe
                85                  90                  95

Arg Leu Asp Tyr Pro Ile Val Lys Cys Lys Val Lys Ser Thr Ile Leu
            100                 105                 110

Arg Glu Cys Lys Glu Tyr Glu Phe Asp Thr Asn Ala Pro Gln Lys Tyr
        115                 120                 125

Gln Trp Phe Asp Val Leu Ser Tyr
    130                 135

<210> SEQ ID NO 9
<211> LENGTH: 39
<212> TYPE: PRT
<213> ORGANISM: Heloderma horridum

<400> SEQUENCE: 9

Gly Ala Phe Ile Met Pro Gly Thr Leu Trp Cys Gly Ala Gly Asn Ala
 1               5                  10                  15

Ala Ser Asp Tyr Ser Gln Leu Gly Thr Glu Lys Asp Thr Asp Met Cys
            20                  25                  30

Cys Arg Asp His Asp His Cys
        35

<210> SEQ ID NO 10
<211> LENGTH: 31
<212> TYPE: PRT
<213> ORGANISM: Rhopilema nomadica

<400> SEQUENCE: 10

Gly Leu Ile Lys Pro Gly Thr Leu Trp Cys Gly Met Gly Asn Asn Ala
 1               5                  10                  15

Glu Thr Tyr Asp Gln Leu Gly Pro Phe Ala Asp Val Asp Ser Cys
            20                  25                  30
```

MAMMALIAN SECRETED GROUP III PHOSPHOLIPASE A$_2$

RELATED APPLICATION

This patent application claims the benefit of U.S. provisional application No. 60/181,765, filed Feb. 11, 2000. This earlier provisional is hereby incorporated by reference.

FIELD OF THE INVENTION

The present invention concerns DNA and peptide sequence encoding a novel mammalian secreted group III sPLA$_2$ and more particularly a novel human secreted group III (hGIII) sPLA$_2$. The invention also concerns the use of this enzyme in methods for screening various chemical compounds.

BACKGROUND

In recent years, it has been realized that phospholipases A$_2$ (PLA$_2$, EC 3.1.1.4) form a superfamily of intracellular and secreted enzymes, which all catalyze the hydrolysis of glycerophospholipids at the sn-2 position to release fatty acids and lysophospholipids (1–4). To date, 8 distinct mammalian secreted phospholipases A$_2$ (sPLA$_2$S) have been cloned and classified into groups I, II, V and X (2, 4–9). Although the biological role of each of these enzymes has not yet been clearly defined, mammalian sPLA$_2$s have been implicated in various physiological and pathophysiological functions including lipid digestion, cell proliferation, neurosecretion, release of proinflammatory lipid mediators, antibacterial defence, cancer and inflammatory diseases (3, 4). The level of identity between the 8 mammalian sPLA$_2$s can be as low as 23% (8), but they have in common a low molecular mass (14–17 kDa), the presence of several disulfides, a similar Ca$^{2+}$-dependent catalytic mechanism, and a well conserved overall three-dimensional structure (10–13).

Numerous sPLA$_2$s have also been described in venoms from both vertebrate and invertebrate animals such as snakes and bees (14, 15). Similar to mammalian sPLA$_2$s, snake venom enzymes have been classified into groups I and II, and they all have a common catalytic mechanism and a very similar three-dimensional structure (1, 10–13). Snake venom sPLA$_2$s are often neurotoxins or myotoxins, but can also promote physiological effects such as cell migration and cell proliferation (14, 16, 17). Using venom sPLA$_2$s as ligands, different types of sPLA$_2$ receptors have been identified (4). These receptors are likely to be involved in venom sPLA$_2$ toxicity, and recent studies have suggested that mammalian sPLA$_2$s can be the normal endogenous ligands (4, 18, 19). Invertebrate venom sPLA$_2$s are also disulfide-rich proteins, but they have a primary structure distinct from mammalian and snake venom sPLA$_2$s, and have been classified into groups III and IX (2, 4). They have been found in bee, scorpion, jellyfish and marine snail venoms (20–25), and the group III bee venom sPLA$_2$ has been the best studied enzyme. This sPLA$_2$ has been cloned (20) and determination of its three-dimensional structure (11) has revealed important differences with group I and II sPLA$_2$s, although the catalytic site is similar to that of vertebrate sPLA$_2$s (13). Interestingly, sPLA$_2$s similar to the bee venom enzyme were discovered in lizard venom (26, 27), indicating that group III sPLA$_2$s also exist in vertebrates, and thus may occur in mammals as well.

SUMMARY OF THE INVENTION

In the last three years, a systematic search for sPLA$_2$ homologs in nucleic databases has allowed the Applicant to clone four novel mammalian sPLA$_2$s that belong to groups II and X (6–8). Using the same strategy, the Applicant identified a human genomic sequence that displays significant homology with the bee venom group II sPLA$_2$. The cloning, genomic organization, chromosomal mapping, tissue distribution, and heterologous expression of the first human group III sPLA$_2$ are disclosed.

Thus, the invention concerns a novel mammalian secreted group III sPLA$_2$. The invention concerns more particularly a mammalian secreted group III sPLA$_2$ constituted by or comprising the sequence of amino acids in the list of sequences under the number SEQ ID No. 2. More particularly, the mammalian secreted group III sPLA$_2$ is a human secreted group III sPLA$_2$.

The invention concerns a nucleic acid molecule comprising or constituted of an encoding nucleic sequence for a mammalian secreted group III sPLA$_2$ or for a fragment of a mammalian secreted group III sPLA$_2$. The invention also concerns a nucleic acid molecule which encodes for the mammalian secreted group III sPLA$_2$ protein or for a fragment of this protein whose amino acid sequence is represented in the list of sequences in the appendix under the number SEQ ID No. 2. The invention relates more particularly to a nucleic acid molecule constituted by or comprising the sequence in the list of sequences in the appendix under the number SEQ ID No. 1. Evidently the invention also concerns nucleotide sequences derived from the above sequence, for example from the degeneracy of the genetic code, and which encode for proteins presenting characteristics and properties of secreted group III sPLA$_2$.

Another aim of the present invention is polyclonal or monoclonal antibodies directed against one secreted group III sPLA$_2$ of the invention, a derivative or a fragment of these. These antibodies can be prepared by the methods described in the literature. According to prior art techniques, polyclonal antibodies are formed by the injection of proteins, extracted from the epithelium or produced by genetic transformation of a host, into animals, and then recuperation of antiserums and antibodies from the antiserums for example by affinity chromatography. The monoclonal antibodies can be produced by fusing myeloma cells with spleen cells from animals previously immunised using the receptors of the invention. These antibodies are useful in the search for new secreted mammalian group III sPLA$_2$ or the homologues of this enzyme in other mammals or again for studying the relationship between the secreted group III sPLA$_2$ of different individuals or species.

The invention also concerns a vector comprising at least one molecule of nucleic acid above, advantageously associated with adapted control sequences, together with a production or expression process in a cellular host of a group III sPLA$_2$ of the invention or a fragment thereof. The preparation of these vectors as well as the production or expression in a protein host of the invention can be carried out by molecular biology and genetic engineering techniques well known to the professional.

An encoding nucleic acid molecule for a mammalian secreted group III sPLA$_2$ or a vector according to the invention can also be used to transform animals and establish a line of transgenic animals. The vector used is chosen in function of the host into which it is to be transferred; it can be any vector such as a plasmid. Thus the invention also relates to cellular hosts expressing mammalian secreted group III sPLA$_2$ obtained in conformity with the preceding processes.

The invention also relates to nucleic and oligonucleotide probes prepared from the molecules of nucleic acid according to the invention. These probes, marked advantageously, are useful for hybridisation detection of similar group III sPLA$_2$ in other individuals or species. According to prior art techniques, these probes are put into contact with a biological sample. Different hybridisation techniques can be used, such as Dot-blot hybridisation or replica hybridisation (Southern technique) or other techniques (DNA chips). Such probes constitute the tools making it possible to detect similar sequences quickly in the encoding genes for group III sPLA$_2$ which allow study of the presence, origin and preservation of these proteins. The oligonucleotide probes are useful for PCR experiments, for example to search for genes in other species or with a diagnostic aim.

The sPLA$_2$ are expressed in a variety of tissues under both normal and pathological conditions (including inflammatory diseases, cancers, cardiac and brain ischemia, etc . . . ) and are involved in a myriad of physiological and pathological roles. These proteins are also involved in cell proliferation, cell migration, angiogenesis, cell contraction, apoptosis, neurosecretion, blood coagulation, adipogenesis, lipid metabolism (digestion, skin lipid barrier and lung surfactant formation, lipoprotein metabolism, . . . ), spermatogenesis, fecondation and embryogenesis. They also play a role in host defense and have antiviral and antibacterial properties against viruses like HIV-1 and various Gram-positive and Gram-negative bacterial strains. They are also involved in various pathological conditions such as acute lung injury, acute respiratory distress syndrome, Crohn's disease and various types of cancers where sPLA$_2$ can act as gene suppressor.

Consequently, this invention can also be useful in methods for identifying biologically active compounds with anti-inflammatory properties or more generally for identifying compounds that modulate sPLA$_2$ biological activities as listed above.

Such biologically active compounds can be identified by determining if a selected compound is capable of inhibiting the catalytic activity of sPLA$_2$ in cleaving a phospholipid to release fatty acids and lysophospholipids in a mixed micelle assay, a liposome assay, a system utilizing natural membranes, or in whole cells overexpressing this enzyme. A compound capable of inhibiting sPLA$_2$ catalytic activity may have anti-inflammatory or may behave as an antagonist of sPLA2 in the sPLA2 biological activities listed above.

For example, screening of compounds for potential anti-inflammatory activity can be performed with the novel sPLA$_2$ enzymes of this invention, purified to homogeneity from cell sources or produced recombinantly or synthetically. A selected compound may be added to a sPLA2 enzyme of this invention in a mixed micelle assay, a liposome assay, or an assay system utilizing natural membranes and analyzed for inhibition of sPLA2 activity. Alternatively, a selected compound may be added to whole cells which overexpress the sPLA$_2$ and the cells examined for inhibition of release of fatty acids or lysophospholipids. In this case, normal cells and cells overexpressing sPLA$_2$ can be cultured in labelled arachidonic acid. Signal is measured between the secreted products of both the normal and overexpressing cells to provide a baseline of sPLA$_2$ expression. A selected compound is then added to cultures and the cultures are grown in label arachidonic acid. If there is a difference in the signal (e.g., the amount of arachidonic acid produced) in the cells in the presence of the compound, this compound inhibits sPLA2 activity and may be a potential anti-inflammatory compound.

Biologically active compounds can also be identified by screening the selected compounds for their binding properties to sPLA$_2$ receptors that bind group III sPLA$_2$s of this invention. These receptors include the family of N-type receptors which are likely to be involved in several biological activities of sPLA$_2$s including HIV-1 antiviral properties. For example, radioactively or fluorescently labeled sPLA$_2$s can be used in competition binding assays and selected compounds can be screened for inhibition of sPLA$_2$ binding.

Biologically active compounds can also be identified by screening the selected compounds for modulation of a sPLA$_2$ biological effect such as those listed above. For example, sPLA$_2$s of this invention may be added to cells in the presence or absence of a selected compound and cells may be assayed for cell proliferation, cell migration, cell contraction or apoptosis.

In general, another aspect of this invention is thus related to the use of a compound first identified by the methods described above. Novel pharmaceutical compositions may contain a therapeutically effective amount of a compound identified by an above method of this invention. These pharmaceutical compositions may be employed in methods for treating disease states or disorders involving group III sPLA$_2$s of this invention.

BRIEF DESCRIPTION OF THE DRAWINGS

Other advantages and characteristics of the invention will become apparent by reading the following examples concerning the cloning, genomic organization, chromosomal mapping, tissue distribution, and heterologous expression of the first human group III sPLA$_2$ and which refer to the attached drawings in which:

FIG. 2 presents the alignment of the amino acid sequences of group III sPLA$_2$s. Sequences of mature sPLA$_2$ proteins are shown. sPLA$_2$ sequences are from (20, 22, 23, 25–27). Only partial sequences have been reported for jellyfish and Mexican beaded lizard sPLA$_2$s (25, 26).

DETAILED DESCRIPTION

I. Experimental Procedures

Figure 1:
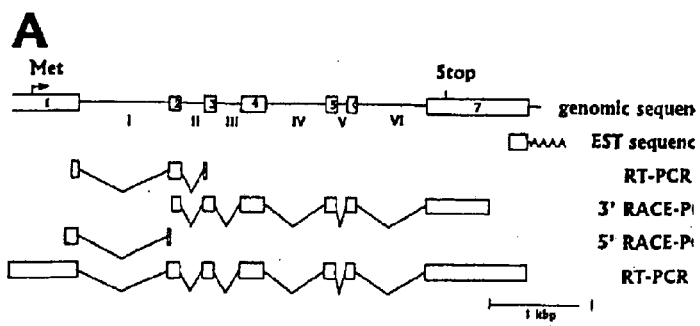
FIG. 1 presents a schematic diagram of the gene (A) and cDNA nude tide sequence (B) of hGIII sPLA$_2$. A, the exon-intron structure of the hGIII sPLA$_2$ gene is shown at the top and below are shown the EST sequence and the different cDNA PCR Products which have been amplified to determine the sequence of the full-length hGIII sPLA$_2$ (Panal B). Exons and introns are represented as open boxes and straight lines, respectively. The methionine initiation codon and stop codon of the hGIII sPLA$_2$ gene are located in exons 1 and 7. The sPLA$_2$ domain is encoded by exons 1 to 4. B, the consensus cDNA sequence is shown. The predicted signal peptide segment is boxed. The five putative N-glycoslyation sites are squared. The sPLA$_2$ domain is underlined. The exon-intron boundaries are indicated by arrowheads.

I.1 Molecular Cloning of hGIII sPLA$_2$.

Searching for sPLA$_2$ homologs in gene databases stored at the National Center for Biotechnology using the tBLASTn sequence alignment program (28) resulted in the identification of a human genomic sequence (PAC clone DJ412A9, GenBank accession number AC005005) of 133893 nucleotides containing several regions of homology to bee venom group III sPLA$_2$. This suggested that this large genomic clone contains a gene with several exons and introns coding for a novel human group III sPLA$_2$. The exon-intron boundaries of the human sPLA$_2$ gene were deduced according to alignment with bee venom sPLA$_2$ and exon-intron consensus sequences (29) to provide a putative cDNA sequence. To demonstrate the presence of the putative cDNA sequence in human tissues, a first set of RT-PCR experiments (RT-PCR 1 in FIG. 1) was performed on different human cDNAs with primers flanking the Ca$_{2+}$-binding loop and the active site domain of the novel sPLA$_2$ (sense and antisense primers correspond to nucleotides 445 to 468 and 655 to 679, respectively, FIG. 1). A DNA product was amplified from human fetal lung cDNA and found to have a nucleotide sequence corresponding to the putative cDNA. This sequence was then used to clone the entire cDNA sequence by 5' and 3' RACE-PCR experiments as previously described (7). Briefly, human fetal lung Poly A+ RNA (2 μg, Clontech) was reverse transcribed, and double stranded cDNA was ligated to adaptors containing sequences for the universal primers SP6 and KS. PCR reactions were performed using KS primer and a specific forward or reverse primer, for 3' or 5' RACE-PCR, respectively. PCR products were subcloned into pGEM-T easy vector (Promega), and colonies were screened using an internal [$^{32}$P]-labeled oligonucleotide probe. 3' RACE-PCR experiments led to the cloning of a 1458 nucleotide sequence that contained in its 3' end an in frame extension of 304 amino acids, a stop codon and a 3' noncoding region of 546 nucleotides containing a putative polyadenylation site. Searching in EST databases resulted in the identification of an EST sequence (Genbank A1282787), and full sequencing of this EST clone revealed a 193 nucleotide sequence containing a 166 nucleotide sequence identical in its 5' end to the genomic clone and a 27 nucleotide polyA sequence. 5' RACE-PCR experiments were performed with an antisense primer (nucleotides 518–545 in FIG. 1) and led to the cloning of a 158 nucleotide sequence, extending the 5' end sequence of the RT-PCR 1 DNA fragment by 20 amino acid residues. In frame with this 158 nucleotide sequence, an initiator methionine followed by a 19 amino acid sequence presenting the features of a signal peptide sequence (30) was found in the upstream genomic sequence. A primer upstream of the putative initiator methionine (nucleotides −254 to −229 in FIG. 1) and an antisense primer (nucleotides 2205 to 2236 in FIG. 1) derived from the above EST sequence were designed and used to amplify the full-length hGIII cDNA sPLA$_2$ (RT-PCR 2 in FIG. 1). This RT-PCR experiment was performed on the same human fetal lung cDNA using the proofreading Pwo DNA Polymerase and led to the cloning of a cDNA fragment of 2564 nucleotides containing an open reading frame of 1530 nucleotides. To confirm that this long open reading frame resulted from a proper splicing of the hGIII sPLA$_2$ gene, exon-trapping experiments were performed. For this purpose, a genomic fragment encompassing the putative hGIII gene was amplified with the Expand long template PCR system (Roche), primers designed from the human PAC clone DJ412A9 (nucleotides 36143–36175 and 43062–43092 for sense and antisense primers, respectively), and human genomic DNA as template. An expected 6.95 kilobase pair genomic fragment was amplified and subcloned into the exon trapping pET01 vector (MoBiTech), partially sequenced, and the resulting plasmid was transfected into COS cells. Three days after transfection, total RNA was prepared, reverse transcribed with oligodT, and submitted to PCR with primers flanking the hGIII sPLA$_2$ open reading frame. A PCR fragment of 1530 nucleotides was amplified, cloned into pGEM-T easy vector (Promega), and found to encode for the full-length hGIII open reading frame. No amplification was observed with cDNA from COS cells transfected with the parent exon-trapping vector.

I.2 Analysis of the Tissue Distribution of hGIII sPLA$_2$.

A human northern blot (Clontech catalog # 7780-1) was probed with a [$^{32}$P]-labeled riboprobe corresponding to the nucleotide sequence 445 to 679 of hGIII sPLA$_2$ (FIG. 1) in ULTRAHyb hybridization buffer (Ambion, catalog # 8670) for 18 h at 70° C. High-sensitivity stripable antisense riboprobe was synthesized using the Strip-EZ RNA Ambion kit (catalog # 1360). The blot was washed to a final stringency of 0.1× SSC (30 mM NaCl, 3 mM trisodium citrate, pH 7.0) in 0.1% SDS at 70° C. and exposed to Kodak Biomax MS films with a transcreen-HE intensifying screen.

II.3 Recombinant Expression of hGIII sPLA$_2$ in COS cells.

The full-length cDNA sequence coding for hGIII sPLA$_2$ was subcloned into the expression vector pRc/CMVneo (Invitrogen) and a consensus Kozak sequence was added to enhance protein expression as previously described (6). The DNA construct was sequenced after subcloning and transiently transfected into COS cells using DEAE-dextran (7). Five days after transfection, cell medium was collected and partially purified on an anion exchange column. Briefly, COS cell culture medium (9 ml) was loaded at 1 ml/min onto a 10 ml column of Q-Sepharose Fast Flow (Pharmacia) previously equilibrated in 25 mM Tris, pH 8.0 at 4° C. After washing with equilibration buffer to remove unbound protein, the solvent program was started (10 min in equilibration buffer followed by a linear gradient of NaCl from 0 to 1 M NaCl over 40 min). hGIII sPLA$_2$ enzymatic activity was detected using the fluorimetric assay with 1-palmitoyl-2-(10-pyrenedecanoyl)-sn-glycero-3-phosphomethanol as described (8). The pool of hGIII-containing fractions was concentrated approximately 10-fold by centrifugal ultrafiltration (YM-10 membrane, Amicon) at 4° C., and the concentrate was stored at −20° C. Using this assay, no phospholipase A$_2$ activity was detected in culture medium from COS cells transfected with the parent expression vector.

I.4 PLA$_2$ Activity Studies.

Studies to measure the initial rate of hydrolysis of small unilamellar vesicles of phosphatidylglycerol (1-palmitoyl-2-([9,10[$^3$H])-palmitoyl-sn-glycero-3-phosphoglycerol in 1-palmitoyl-2-oleoyl-sn-glycero-3-phosphoglycerol at 50 Ci/mol) and phosphatidylcholine (1-palmitoyl-2-([9,10[$^3$H])-palmitoyl-sn-glycero-3-phosphocholine, 50 Ci/mol) were carried as described (8) using Q-Sepharose purified hGIII sPLA$_2$. Initial rates were calculated from 3 time points in the linear portion of the product versus time curve. pH-rate profiles for the hydrolysis of phosphatidylcholine were obtained as described (8). The Ca$^{2+}$ dependency of phospholipid hydrolysis was carried out with the fluorimetric assay (described above) with 10 μM EGTA (no Ca$^{2+}$) or with CaCl$_2$ in excess of EGTA to give 10–650 μM Ca$^{2+}$.

II. Results.

II.1 Molecular Cloning of hGIII sPLA$_2$.

Screening of mammalian nucleic sequence databases with various venom sPLA$_2$s led us to identify a large human genomic fragment of 133893 nucleotides presenting several regions of homology with bee venom group III sPLA$_2$. This suggested that the genomic clone contains a complete gene with several exons and introns coding for a putative human group III (hGIII) sPLA$_2$. A first set of sense and antisense primers was designed from the genomic sequences homologous to bee venom sPLA$_2$ and used for RT-PCR experiments (RT-PCR 1 in FIG. 1A) on human cDNAs from brain, pancreas, spleen, skeletal muscle, and fetal lung. A DNA fragment was amplified from fetal lung cDNA and its sequence was found to correspond to the expected spliced exons from the genomic sequence. 5' and 3' RACE-PCR experiments followed by a second round of RT-PCR (RT-PCR 2 in FIG. 1A) on human fetal lung cDNA led to the cloning of a cDNA fragment of 2564 nucleotides containing a large open reading frame of 1530 nucleotides (see FIG. 1 and Experimental Procedures for details). Screening of EST databases resulted in the identification of a single human EST sequence (Genbank A1282787) of 193 nucleotides containing a polyA tail, suggesting that this EST sequence corresponds to the 3' end of the hGIII sPLA$_2$ mRNA (FIG. 1A). Comparison of the 2564 nucleotide cDNA sequence with the PAC genomic sequence indicated that the hGIII sPLA$_2$ gene is composed of at least 7 exons and 6 introns spanning about 7 kilobase pairs (FIG. 1A). Exon-trapping experiments were performed and found to confirm the exon-intron structure and the sequence of the complete hGIII sPLA$_2$ open reading frame of 1530 nucleotides (see Experimental Procedures). The PAC clone DJ412A9 (Genbank AC005005) containing the hGIII sPLA$_2$ gene was generated by the sequencing program of human chromosome 22 (31), indicating that the hGIII sPLA$_2$ gene maps to this chromosome between the Genethon markers D22S1150 and D22S273. The location of the hGIII gene is thus distinct from those of genes for human group IB, IIA, IID, V and X sPLA$_2$s (8, 9).

Figure 2:
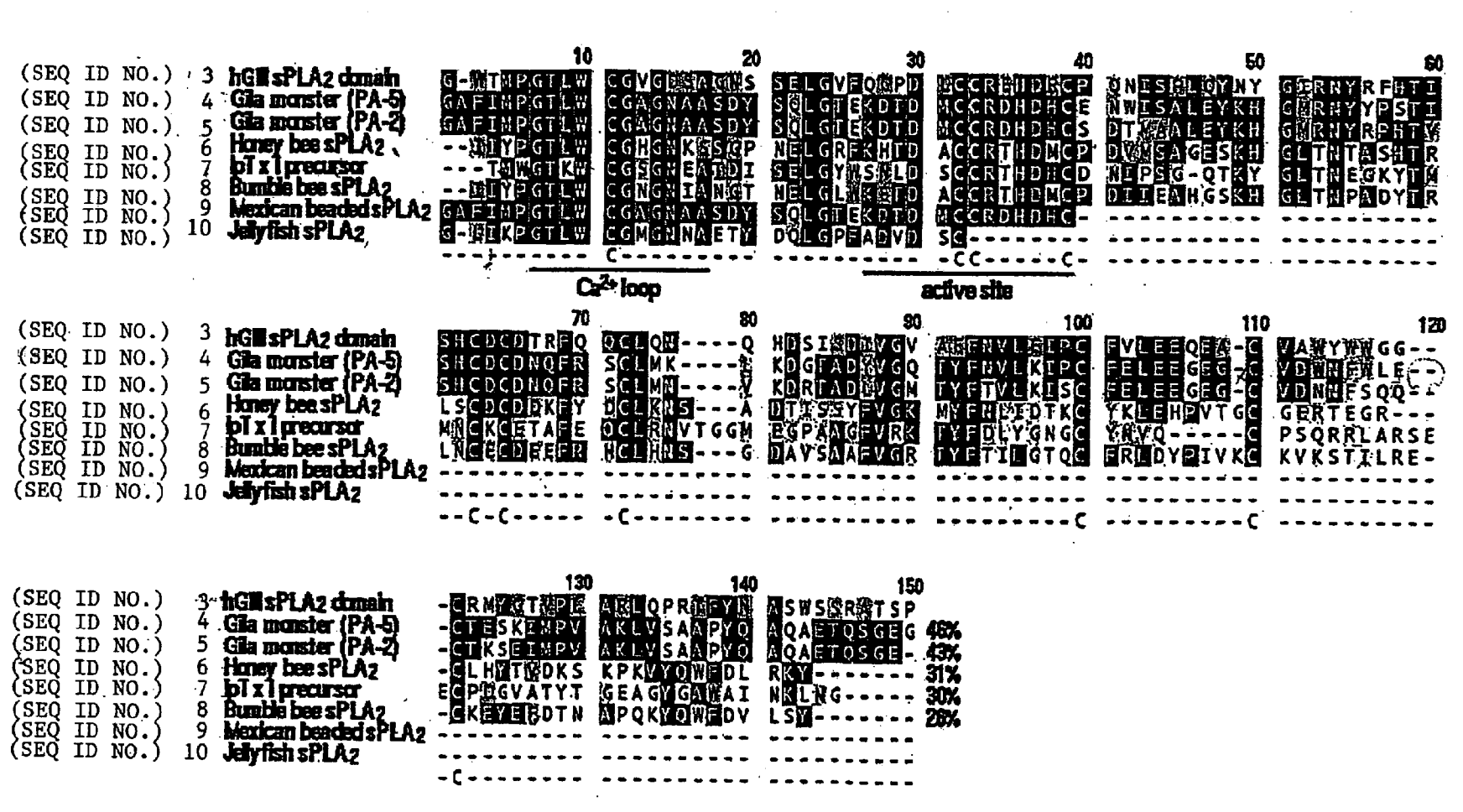

Similar to other mammalian sPLA$_2$s, the open reading frame of hGIII sPLA$_2$ begins with a signal peptide of 19 amino acids (30), indicating that the novel enzyme could be secreted. In contrast to other mammalian sPLA$_2$s (117 to 148 amino acids), the hGIII open reading frame codes for a much larger protein of 490 amino acids (calculated molecular mass 55.3 kDa, calculated pI 9.1) containing five putative N-glycosylation sites (FIG. 1B). This protein is made up of a central sPLA$_2$ domain (141 residues) flanked by N- and C-terminal regions (130 and 219 residues, respectively). Based on the alignment with venom group III sPLA$_2$s (FIG. 2), the sPLA$_2$ domain comprises 141 amino acids (calculated molecular mass 16 kDa, calculated pI 5.4) and displays the typical features of group III sPLA$_2$s including the 10 cysteines specific for group III sPLA$_2$s and the key residues of the Ca$^{2+}$-loop and catalytic site. The sPLA$_2$ domain contains 2 putative N-glycosylation sites which are not conserved with that of bee venom sPLA$_2$ located at position 15 in FIG. 2. However, one of them is located only 4 residues downstream of the glycosylation site in bee venom sPLA$_2$. Interestingly, the hGIII domain is more similar to venom group III sPLA$_2$s identified from vertebrates. Indeed, higher levels of identity are found with the isoforms PA-2 and PA-5 (43 and 46%, respectively) purified from the lizard Gila monster (27), while lower levels are observed with venom group III sPLA$_2$s from honey bee, bumble bee and the scorpion *Pandinus imperator* (FIG. 2).

No protein database entries with significant homology to the N- and C-terminal regions flanking the sPLA$_2$ domain of the hGIII sPLA$_2$ gene could be found. They are both basic (calculated pI 9.1 and 11.3 for N- and C-terminal regions, respectively) and contain 4 and 8 cysteines, suggesting that they may fold separately from the sPLA$_2$ domain. The function of these two domains are completely unknown at present. One possibility is that these domains could be involved in the maturation of hGIII sPLA$_2$ during or after its secretion from cells. Although the maturation processing of hGIII sPLA$_2$ clearly remains to be elucidated, the presence of a basic doublet KR at the end of the N-terminal domain (FIG. 1B) suggests that this domain could serve as a long propeptide that can be cleaved by subtilisin-like protein convertase in the Golgi apparatus (32). Interestingly, the mature protein sequence of bee venom sPLA$_2$ is preceded by an arginine residue (20) and a short propeptide sequence ending with an arginine doublet has been found in human group X sPLA$_2$ (6). The C-terminal region also contains several basic residues including basic doublets, which may be involved in protein maturation as well. In addition, the C-terminal domain contains numerous prolines and a pentapeptide RRLAR similar to that found in Imperatoxin I from *Pandinus imperator* venom (22). In this regard, it is not yet clear whether some venom group III sPLA$_2$s also have such large N- and C-terminal regions, since only mature protein sequences and partial cDNA sequences have been determined so far (20, 23, 25–27), except for the *Pandinus imperator* venom sPLA$_2$s (22, 24). A second possibility may be that the N- and C-terminal domains are involved in sPLA$_2$ dimerization, cell targeting or interaction with cellular proteins possibly including sPLA$_2$ receptors (4). The last possibility may be that these domains play a role in regulating hGIII sPLA$_2$ activity. Unlike group I and II sPLA$_2$S which contain a hydrogen bond network linking the N-terminus to catalytic residues, the X-ray structure of bee venom sPLA$_2$ shows that the N-terminus does not form part of the active site structure (11). Indeed, recombinant bee venom sPLA$_2$ expressed as an N-terminal fusion protein exhibits the same catalytic activity as the cleaved fusion or the native enzyme (33). This suggests that the presence of the N-terminal extension (and presumably the C-terminal region which is also not part of the catalytic site (11)) would not interfere with the catalytic activity of hGIII sPLA$_2$. Full-length or partially cleaved hGIII sPLA$_2$ may thus be catalytically active and N-and C-terminal domains may participate to the hGIII enzymatic properties. Further studies are clearly needed to elucidate the maturation process of the hGIII sPLA$_2$ protein and the role of these additional N- and C-terminal regions.

II.2 Tissue Distribution of hGIII sPLA$_2$.

Figure 3:
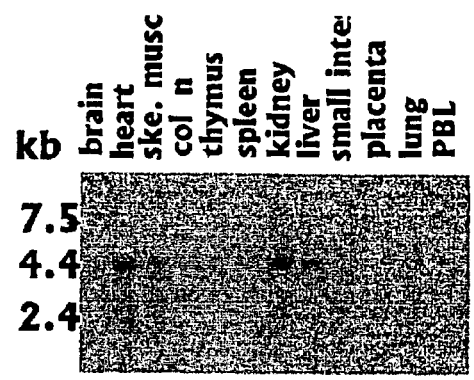
FIG. 3 presents a Northern blot analysis of the tissue distribution of hGIII sPLA$_2$. A commercial northern blot containing 2 μg of poly A+RNA from different human adult tissues was hybridized at high stringency with [$_{32}$P]-labeled sPLA$_2$ RNA probe as described under "Experimental Procedures". sk. musc., skeletal muscle; small intest., small intestine; PBL, peripheral blood leukocytes. kb, kilobase. The blot was exposed for 7 days.

The tissue distribution of hGIII sPLA$_2$ was analyzed by hybridization at high stringency to a human northern blot (FIG. 3). The hGIII sPLA$_2$ is expressed as a single transcript of 4.4 kilobase which is abundant in kidney, heart, liver and skeletal muscle, and is also present at low levels in placenta and peripheral blood leukocytes. Little, if any, expression was detected in brain, colon, thymus, spleen, small intestine and lung. The pattern of expression of hGIII sPLA$_2$ is distinct from that of other human sPLA$_2$s, suggesting that this novel enzyme has specific function(s). Notably, hGIII sPLA$_2$ is expressed in kidney while no expression was previously detected in this tissue for human group IB, IIA, IID, V and X sPLA$_2$s (6, 9). On the other hand, hGIII sPLA$_2$ is co-expressed in heart with human group IIA and V sPLA$_2$s, and in liver and skeletal muscle with human group IIA sPLA$_2$ (6).

I.3 Recombinant Expression of hGIII sPLA$_2$ and Enzymatic Properties.

When the hGIII sPLA$_2$ cDNA was transiently transfected in COS cells, sPLA$_2$ activity accumulated in the culture medium, indicating that the hGIII sPLA$_2$ cDNA codes for a secreted active enzyme. The level of PLA$_2$ activity measured after washing the cells with high salt buffer containing 1 M NaCl and in cell lysate was low, suggesting that hGIII sPLA$_2$ is not tightly bound to the cell surface and is efficiently secreted. The hGIII sPLA$_2$ was partially purified by chromatography on a Q-Sepharose fast flow column and the eluted sPLA$_2$ fraction was used to analyze the enzymatic properties.

Figure 4:
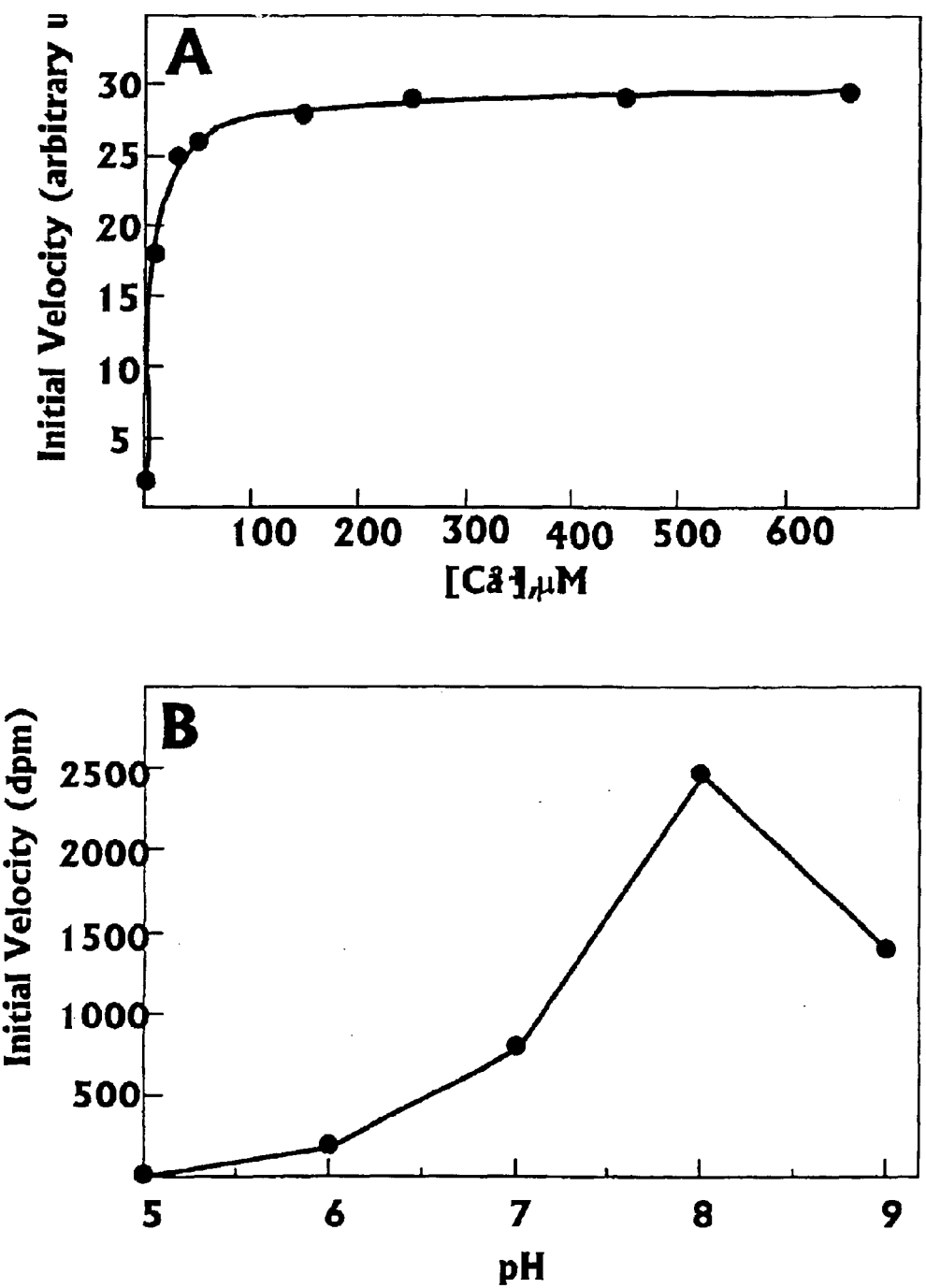
FIG. 4 presents the enzymatic properties of hGIII sPLA$_2$. A, Ca$^{2+}$ dependency of the hydrolysis of 1 -palmitoyl-2-(10-pyrenedecanoyl)-sn-glycerol-3- phosphomethanol vesicles by Q-sepharose purified hGIII sPLA$_2$. B, pH dependency of the hydrolysis of phosphatidylcholne vesicles by Q-Sepharose purified gGIII sPLA$_2$.

Like all mammalian sPLA$_2$s that have been kinetically characterized (7, 8, 34, 35), hGIII sPLA$_2$ is considerably more active (11-fold based on initial velocities) on anionic phosphatidylglycerol vesicles versus zwitterionic phosphatidylcholine vesicles (not shown). Further studies with pure hGIII sPLA$_2$ in larger quantities are required to determine if this rate difference is due to an increased fraction of enzyme bound to the anionic versus zwitterionic interface, a lower value of the interfacial KM for phosphatidylglycerol versus phosphatidylcholine, or both. As shown in FIG. 4A, the rate of phosphatidylmethanol vesicle hydrolysis by hGIII is completely $Ca^{2+}$-dependent with a Kd of 6±0.8 $\mu$M. The Kd for $Ca^{2+}$ of 6 $\mu$M for the action of hGIII sPLA$_2$ on phosphatidylmethanol vesicles is considerably lower than the sub-millimolar to millimolar values reported for other sPLA$_2$S. However, the Kd value measured in this study is an apparent value. For sPLA$_2$s, phospholipid binding to the active site is $Ca^{2+}$ dependent, and thus the observed apparent Kd for $Ca^{2+}$ depends on the affinity of enzyme's active site for phospholipid substrate (36). Kd for $Ca^{2+}$ is also modulated by the affinity of the enzyme for the vesicle interface since interfacial binding is a prerequisite for the binding of long-chain phospholipids to the enzyme's active site. In this context, it may be noted that human group IIA sPLA$_2$ binds $Ca^{2+}$ with millimolar affinity in the absence of substrate (37, 38), but the Kd for $Ca^{2+}$ in the presence of phosphatidylglycerol (which supports tight interfacial and active site binding) is in the low micromolar range (39). Once large amounts of recombinant hGIII sPLA$_2$ are available, it will be possible to use spectroscopic methods to measure the affinity of the enzyme for $Ca^{2+}$ in the absence of substrate. As shown in FIG. 4B, hGIII sPLA$_2$ is optimally active on phosphatidylcholine vesicles at pH 8. The pH-rate profile of hGIII is similar to most sPLA$_2$s (12). The increase in rate up to pH 8 probably reflects deprotonation of the active site histidine so that it can function as a general base for the attack of a water molecule on the substrate ester carbonyl group (13).

II.4 Summary

Over the past few years, the molecular biology approach has revealed the presence of a diversity of sPLA$_2$s in mammals (5–9). The mammalian sPLA$_2$ family comprises eight members of 14–17 kDa including a group 1, 5 group II, a group V and a group X sPLA$_2$s. It also includes otoconin-95, a major protein of the extracellular otoconial complex of inner ear, which consists of a large secreted protein of 469 residues containing two sPLA$_2$-like domains (40, 41). All these sPLA$_2$s have a conserved primary structures, have in common various disulfide, and several have a similar genomic organization. These sPLA$_2$s are thus structurally-related enzymes that fall within the same set of proteins, namely the I/II/V/X sPLA$_2$ collection. It should be noted however that they all have distinct tissue distribution and function. The mammalian sPLA$_2$ family now also comprises the human group III sPLA$_2$ which does not belong to the I/II/V/X sPLA$_2$ collection. hGIII sPLA$_2$ has a distinct sPLA$_2$ primary sequence from the above sPLA$_2$s, contains extra N- and C-terminal regions, and has a different genomic organization. Together, this indicates that mammals can express sPLA$_2$s of the group I/II/V/X collection and of the distinct group III collection. Interestingly, the same can be observed in reptiles, since sPLA$_2$s found in snake venoms are group I or II enzymes while those found in lizard venoms belong to group III (15). In addition, as previously pointed out (15), it is likely that a single snake species can express several sPLA$_2$s from different groups which are present in various tissues other than the venom gland. Finally, while most sPLA$_2$s reported so far in the venom of invertebrates appear to be group III enzymes (20, 22–25), scanning of nucleic databases indicates that invertebrates also express sPLA$_2$s from the group I/II/V/X collection in other tissues. In short, this makes likely that both vertebrates and invertebrates express a variety of sPLA$_2$s of the group I/II/V/X collection and of group III, and that these sPLA$_2$S are present in various tissues to deserve specific functions. Lastly, based on the current sPLA$_2$s found in mammals, it is tempting to speculate that vertebrates have "chosen" to generate a sPLA$_2$ diversity from the group I/II/V/X collection and not from the group III collection. It remains however to determine if more than one group III sPLA$_2$ is expressed in mammals, and if reptiles and invertebrates have made the same "choice" to make their own sPLA$_2$ diversity.

In conclusion, a novel human sPLA$_2$ that clearly belongs to group III was cloned. This sPLA$_2$ seems to have a number of distinct structural features compared to the known venom group III sPLA$_2$s, suggesting that hGIII sPLA$_2$ may not be the structural "equivalent" of these venom sPLA$_2$s (4). Its tissue distribution appears non redundant with other human sPLA$_2$s, suggesting particular function(s). Our initial survey indicate a strong expression of hGIII sPLA$_2$ in heart, kidney, liver and skeletal muscle, but a more extensive analysis in a wide variety of tissues, cell types and extracellular fluids under both normal and pathological conditions could emphasize unsuspected sPLA$_2$ functions. So far, sPLA$_2$s have been found in many tissues and cells, and their functions are only slowly being discovered. Some of them have been implicated as potent mediators of inflammation and their levels are elevated in numerous inflammatory diseases and after challenge by proinflammatory cytokines and endotoxins (3, 4, 9, 42). Levels of sPLA$_2$s are also increased in cancer and sPLA$_2$s have been proposed to play a role in cell proliferation and cancer (3, 4, 9). sPLA$_2$s are also increased after ischemia (3, 43) and they may play a role in neurotransmission (44). Finally, sPLA$_2$s have been involved in host defense mechanisms against different bacterial strains (45–48) and more recently, sPLA$_2$s including bee venom group III have been revealed to be potent human immunodeficiency virus type 1 inhibitors (49).

References

1. Dennis, E. A. (1994) *J. Biol. Chem.* 269, 13057–13060
2. Dennis, E. A. (1997) *Trends Biol. Sci.* 22,1–2
3. Murakami, M., Nakatani, Y., Atsumi, G., Inoue, K., and Kudo, I. (1997) *Crit. Rev. Immunol.* 17, 225–283
4. Lambeau, G., and Lazdunski, M. (1999) *Trends Pharmacol. Sci.* 20,162–170
5. Tischfield, J. A. (1997) *J. Biol. Chem.* 272, 17247–17250
6. Cupillard, L., Koumanov, K., Mattéi, M. G., Lazdunski, M., and Lambeau, G. (1997) *J. Biol. Chem.* 272, 15745–15752
7. Valentin, E., Koduri, R. S., Scimeca, J.-C., Carle, G., Gelb, M. H., Lazdunski, M., and Lambeau, G. (1999) *J. Biol. Chem.* 274, 19152–19160

8. Valentin, E., Ghomashchi, F., Gelb, M. H., Lazdunski, M., and Lambeau, G. (1999) *J. Biol. Chem.* 274, 31195–31202
9. Ishizaki, J., Suzuki, N., Higashino, K., Yokota, Y., Ono, T., Kawamoto, K., Fujii, N., Arita, H., and Hanasaki, K. (1999) *J. Biol. Chem.* 274, 24973–24979
10. Wery, J. P., Schevitz, R. W., Clawson, D. K., Bobbift, E. R., Dow, E. R., Gamboa, G., Goodson, T., Hermann, J., R. B., Kramer, R. M., McClure, D. B., Michelich, E. D., Putnam, J. E., Sharp, J. D., Stark, D. H., Teater, C., Warrick, M. W., and Jones, N. D. (1991) *Nature* 352, 79–82
11. Scott, D. L., Otwinowski, Z., Gelb, M. H., and Sigler, P. B. (1990) *Science* 250, 1563–1566
12. Gelb, M. H., Jain, M. K., Hanel, A. M., and Berg, O. G. (1995) *Annu. Rev. Biochem.* 64, 653–688
13. Scott, D. L., White, S. P., Otwinowski, Z., Yuan, W., Gelb, M. H., and Sigler, P. B. (1990) *Science* 250, 1541–1546
14. Kini, R. M., and Evans, H. J. (1989) *Toxicon* 27, 613–635
15. Davidson, F. F., and Dennis, E. A. (1990) *J. Mol. Evol.* 31, 228–238
16. Kundu, G. C., and Mukherjee, A. B. (1997) *J. Biol. Chem.* 272, 2346–2353
17. Rufini, S., Cesaroni, M. P., Balestro, N., and Luly, P. (1996) *Biochem. J.* 320, 467–472
18. Ohara, O., Ishizaki, J., and Arita, H. (1995) *Prog. Lip. Res.* 34, 117–138
19. Cupillard, L., Mulherkar, R., Gomez, N., Kadam, S., Valentin, E., Lazdunski, M., and Lambeau, G. (1999) *J. Biol. Chem.* 274, 7043–7051
20. Kuchler, K., Gmachl, M., Sippl, M. J., and Kreil, G. (1989) *Eur. J. Biochem.* 184, 249–254
21. McIntosh, J. M., Ghomashchi, F., Gelb, M. H., Dooley, D. J., Stoehr, S. J., Giordani, A. B., Naisbitt, S. R., and Olivera, B. M. (1995) *J. Biol. Chem.* 270, 3518–3526
22. Zamudio, F. Z., Conde, R., Arevalo, C., Becerril, B., Martin, B. M., Valdivia, H. H., and Possani, L. D. (1997) *J. Biol. Chem.* 272,1188611894
23. Hoffman, D. R., and Jacobson, R. S. (1996) *J. Allergy Clin. Immunol.* 97, 812–821
24. Conde, R., Zamudio, F. Z., Becerril, B., and Possani, L. D. (1999) *FEBS Lett.* 460, 447–450
25. Lotan, A., Fishman, L., Loya, Y., and Zlotkin, E. (1995) *Nature* 375, 456
26. Sosa, B. P., Alagon, A. C., Martin, B. M., and Possani, L. D. (1986) *Biochemistry* 25, 2927–2933
27. Vandermeers, A., Vandermeers-Piret, M. C., Vigneron, L., Rathe, J., Stievenart, M., and Christophe, J. (1991) *Eur. J. Biochem.* 196, 537–544
28. Altschul, S. F., Gish, W., Miller, W., Myers, E. W., and Lipman, D. J. (1990) *J. Mol. Biol.* 215, 403–410
29. Guthrie, C. (1991) *Science* 253,157–163
30. Nielsen, H., Engelbrecht, J., Brunak, S., and von Heijne, G. (1997) *Protein Eng.* 10, 1–6
31. Dunham, I., Shimizu, N., Roe, B. A., Chissoe, S., Hunt, A. R., Collins, J. E., Bruskiewich, R., Beare, D. M., Clamp, M., Smink, L. J., Ainscough, R., Almeida, J. P., Babbage, A., Bagguley, C., Bailey, J., Barlow, K., Bates, K. N., Beasley, O., Bird, C. P., Blakey, S., Bridgeman, A. M., Buck, D., Burgess, J., Burrill, W. D., and O'Brien, K. P. (1999) *Nature* 402, 489–495
32. Halban, P. A., and Irminger, J. -C. (1994) *Biochem. J.* 299, 1–18
33. Dudler, T., Chen, W. Q., Wang, S., Schneider, T., Annand, R. R., Dempcy, R. O., Crameri, R., Gmachl, M., Suter, M., and Gelb, M. H. (1992) *Biochim. Biophys. Acta* 1165, 201–210
34. Han, S. K., Kim, K. P., Koduri, R., Bittova, L., Munoz, N. M., Leff, A. R., Wilton, D. C., Gelb, M. H., and Cho, W. (1999) *J. Biol. Chem.* 274,11881–11888
35. Baker, S. F., Othman, R., and Wilton, D. C. (1998) *Biochemistry* 37, 13203–13211
36. Yu, B. Z., Berg, O. G., and Jain, M. K. (1993) *Biochemistry* 32, 6485–6492
37. Franken, P. A., Van den Berg, L., Huang, J., Gunyuzlu, P., Lugtigheid, R. B., Verheij, H. M., and De Haas, G. H. (1992) *Eur. J. Biochem.* 203, 89–98
38. Bayburt, T., Yu, B. Z., Lin, H. K., Browning, J., Jain, M. K., and Gelb, M. H. (1993) *Biochemistry* 32, 573–582
39. Marshall, L. A., and McCarte-Roshak, A. (1992) *Biochem. Pharmacol.* 44, 1849–1858
40. Wang, Y., Kowalski, P. E., Thalmann, I., Ornitz, D. M., Mager, D. L., and Thalmann, R. (1998) *Proc. Natl. Acad. Sci. USA* 95, 15345–15350
41. Verpy, E., Leibovici, M., and Petit, C. (1999) *Proc. Natl. Acad. Sci. USA* 96, 529–534
42. Pruzanski, W., and Vadas, P. (1991) *Immunol. Today* 12, 143–146
43. Lauritzen, I., Heurteaux, C., and Lazdunski, M. (1994) *Brain Res.* 651, 353–356
44. Kolko, M., DeCoster, M. A., de Turco, E. B., and Bazan, N. G. (1996) *J. Biol. Chem.* 271, 32722–32728
45. Harwig, S. S., Tan, L., Qu, X. D., Cho, Y., Eisenhauer, P. B., and Lehrer, R. I. (1995) *J. Clin. Invest.* 95, 603–610
46. Murakami, M., Tada, K., Nakajima, K., and Kudo, I. (1997) *J Immunol* 159, 439–46
47. Qu, X. D., and Lehrer, R. I. (1998) *Infect. Immun.* 66, 2791–2797
48. Dominiecki, M. E., and Weiss, J. (1999) *Infect. Immun.* 67, 2299–2305
49. Fenard, D., Lambeau, G., Valentin, E., Lefebvre, J. C., Lazdunski, M., and Doglio, A. (1999) *J. Clin. Invest* 104, 611–618

What is claimed is:

1. An isolated mammalian group III secreted phospholipase A$_2$ (sPLA$_2$) comprising the sequence of amino acids as set forth in SEQ ID No. 2.

* * * * *